(12) United States Patent
Chun

(10) Patent No.: US 7,963,939 B2
(45) Date of Patent: Jun. 21, 2011

(54) SYRINGE HAVING EXTENDED BLENDING PATH

(76) Inventor: Thomas Chun, Northridge, CA (US)

( * ) Notice: Subject to any disclaimer, the term of this patent is extended or adjusted under 35 U.S.C. 154(b) by 95 days.

(21) Appl. No.: 12/429,985

(22) Filed: Apr. 24, 2009

(65) Prior Publication Data

US 2010/0274184 A1 Oct. 28, 2010

(51) Int. Cl.
*A61M 37/00* (2006.01)
*G05D 7/01* (2006.01)
(52) U.S. Cl. .................. 604/88; 138/43; 604/91
(58) Field of Classification Search .......... 604/82–92; 138/42, 43, 46
See application file for complete search history.

(56) References Cited

U.S. PATENT DOCUMENTS

| | | | | |
|---|---|---|---|---|
| 1,070,226 A * | 8/1913 | Becker | ............ | 138/46 |
| 2,021,079 A * | 11/1935 | Mittendorf et al. | ............ | 138/42 |
| 2,146,823 A * | 2/1939 | Karmazin | ............ | 138/42 |
| 2,248,469 A * | 7/1941 | Smith | ............ | 604/87 |
| 2,490,553 A * | 12/1949 | Smith | ............ | 604/89 |
| 2,588,555 A * | 3/1952 | Molloy | ............ | 251/120 |
| 2,604,119 A * | 7/1952 | Hughes | ............ | 138/43 |
| 3,857,392 A * | 12/1974 | Ogle | ............ | 604/91 |
| 4,411,292 A * | 10/1983 | Schiller | ............ | 138/42 |
| 4,767,415 A * | 8/1988 | Duffy | ............ | 604/232 |
| 5,423,791 A * | 6/1995 | Bartlett | ............ | 604/403 |
| 5,637,087 A * | 6/1997 | O'Neil et al. | ............ | 604/82 |
| 5,876,372 A * | 3/1999 | Grabenkort et al. | ............ | 604/89 |
| 6,425,499 B1 * | 7/2002 | Guiffray | ............ | 222/137 |
| 6,602,223 B2 * | 8/2003 | Szapiro et al. | ............ | 604/89 |
| 6,976,983 B2 * | 12/2005 | Russell | ............ | 604/891.1 |
| 7,325,572 B2 * | 2/2008 | Schinazi et al. | ............ | 138/43 |

* cited by examiner

*Primary Examiner* — Nicholas D Lucchesi
*Assistant Examiner* — Nathan R Price
(74) *Attorney, Agent, or Firm* — James A. Italia; Italia IP

(57) ABSTRACT

An injection device such as a syringe, which has a helical flow path for a solution in which the solvent and solute have been introduced. The helical flow path is formed by a helically configured member which has general overall configuration of a helical coil spring. Individual coils may be formed to have a groove located along the length of the helix. When compressed, the novel member effectively takes on a cylindrical outer configuration. Because the groove is covered and sealed by the surface of the next turn of the helix when compressed, an enclosed helical flow path is formed in the compressed member. The invention may be an injection device using the novel flow path forming member or alternatively, the flow path forming member itself.

16 Claims, 9 Drawing Sheets

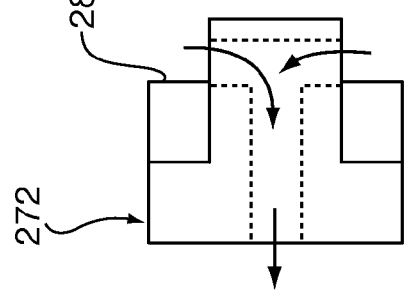
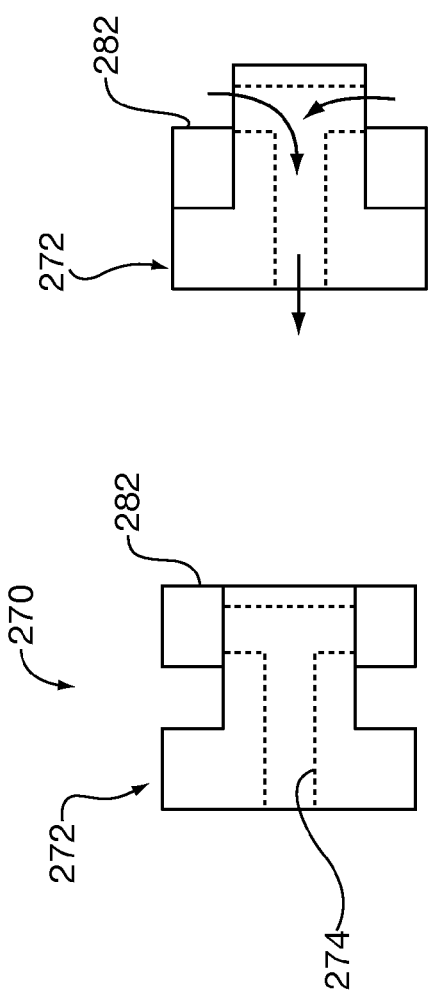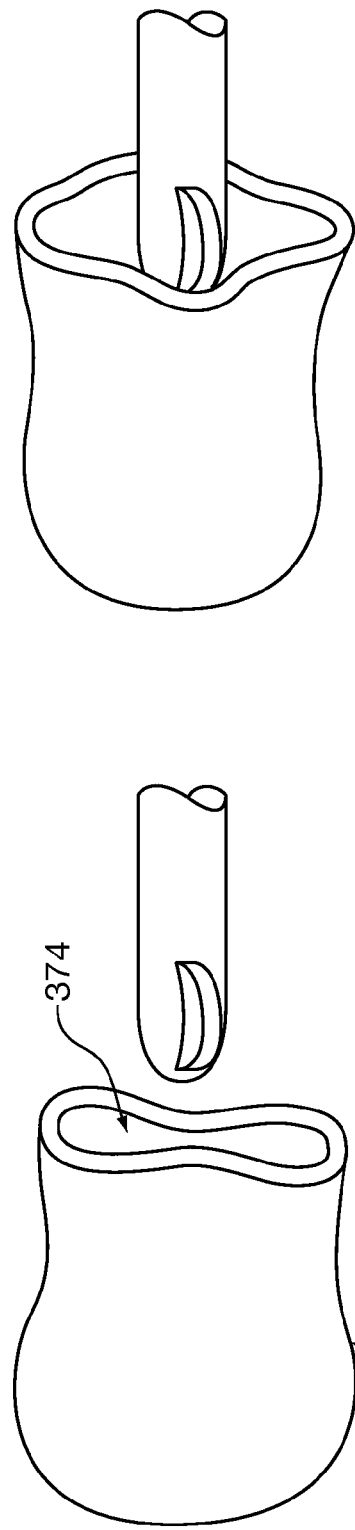

SYRINGE HAVING EXTENDED BLENDING PATH

BACKGROUND OF THE INVENTION

The present invention relates to injection devices such as syringes, and more particularly to an arrangement providing an extended path for effective blending of a liquid solvent and a solid solute within the injection device.

SUMMARY

Injection devices such as syringes are occasionally utilized to deliver liquid substances which are prepared at the last minute from solids. For example, a powdered or granular solid may be loaded into an injection device and blended with a liquid solvent within the injection device at the time of injection.

There exist potential problems with delivery of fully blended solutions. One potential problem is that some substances have short life times once blended with solvents, or may present problems such as precipitation from the solution over time if prepared in advance. Another potential problem is that effective dissolving of the solid solute may possibly be incomplete. This may result in incorrect dosage or in wasteful use of potentially expensive pharmaceutical substances.

As with many medical devices, injection devices entail expense. Especially with medical devices intended to be discarded after a single use, ever more complication is undesirable as it increases costs.

There is a need in the prior art for injection devices which offer effective last minute blending of solid solutes with liquid solvents, yet are inexpensive.

The present invention answers the above stated need by providing an effective yet inexpensive mechanism for enhancing ability of an injection device to dissolve solid solute at the time of injection. In this type of injection device, a supply of liquid solvent is maintained apart from a supply of solid solute. At the time of injection, the supply of liquid solvent is released to flow through and past the solid solute, the former dissolving the latter in so doing.

In the novel approach, there is provided a helical flow path for a solution in which the solvent and solute have been introduced. The flow path is provided between the point of introduction of the liquid solvent and the solid solute and the injecting needle. The helical flow path greatly extends the effective length of the flow path within a relatively short distance within the barrel of the injection device. This promotes progressively increasing dissolution of the solid solute within the solvent.

The helical flow path is provided by an advantageous construction which requires minimally expensive fabrication. Rather than forming a component of fixed geometry, such as a barrel shaped member incorporating a complicated internal passage, an inexpensively fabricated component is provided which is readily reconfigured to provide equivalent internal construction. The internal construction provides the same effectiveness of the desired flow path, but without the expense associated with the fixed geometry part.

The novel member comprises a helically configured member which has general overall configuration of a helical coil spring. Rather than having a solid, circular configuration in cross section as is typical of coil spring wire, the corresponding cross section in the present invention incorporates a flow path. The novel member may be fabricated from an inexpensive flexible material such as a synthetic resin, which enables the novel member to be stretched out axially to a certain degree, and to be collapsed or compressed. When compressed, the novel member effectively takes on a configuration equivalent to the solid component of fixed geometry described above. However, fabrication costs are those of a far less complicated construction, notably, potentially being an extrusion of a linear member having suitable shaping to define a flow path.

In one exemplary configuration, the cross section corresponding to the solid, circular configuration of coil spring wire is square or rectangular, with a groove formed on one exterior surface of the square or rectangle. Arbitrarily describing the groove as being formed in the top surface of the square or rectangle, upon compression of the helix, the groove will be closed by the bottom surface of the next turn of the helix. Thus there is formed a helical groove extending the full length of the compressed helix. Because the groove is covered and sealed by the surface of the next turn of the helix, an enclosed flow path is formed which extends the length of the helical groove. This helical flow path greatly increases the distance which must be negotiated by solvent and solute prior to entering the needle of the injection device. More intimate blending than would occur with straight flow paths occurs.

In another exemplary configuration, no groove is provided. A flow path is nonetheless established due to action of pressure on the fluid which is forced through the helix.

The helical member may be inexpensively fabricated and installed into a generally conventional injection device. The helical member may be held in the compressed configuration after assembly so that it effectively serves as a solid member having a helical internal flow passage.

This construction not only promotes effective blending by maximizing flow path length, but also enables internal components of an injection device, such as a plunger, to be moved into close abutment with the flow path component, so that a high percentage of the liquid solution is successfully discharged during injection. This results in efficient use of the blended solution.

It is therefore an object of the invention to promote more effective dissolution and blending of a solid solute with a liquid solvent when injecting a liquid using an injection device.

It is another object of the invention to minimize costs associated with structure which promotes blending and of other structure of an injection device.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 10 is a cross sectional view of a valve which may be utilized as part of an injection device according to at least one aspect of the invention, shown in the closed condition.

FIG. 11 is a cross sectional view of the valve of FIG. 10, shown in the open condition.

FIG. 12 is a detail side perspective view of a barrier device which may serve as a valve for an injection device according to at least one aspect of the invention and an actuator for opening the barrier device, with the barrier device shown in the closed condition.

FIG. 13 is similar to FIG. 12, but shows the barrier device in the open condition.

DETAILED DESCRIPTION

Figure 1:
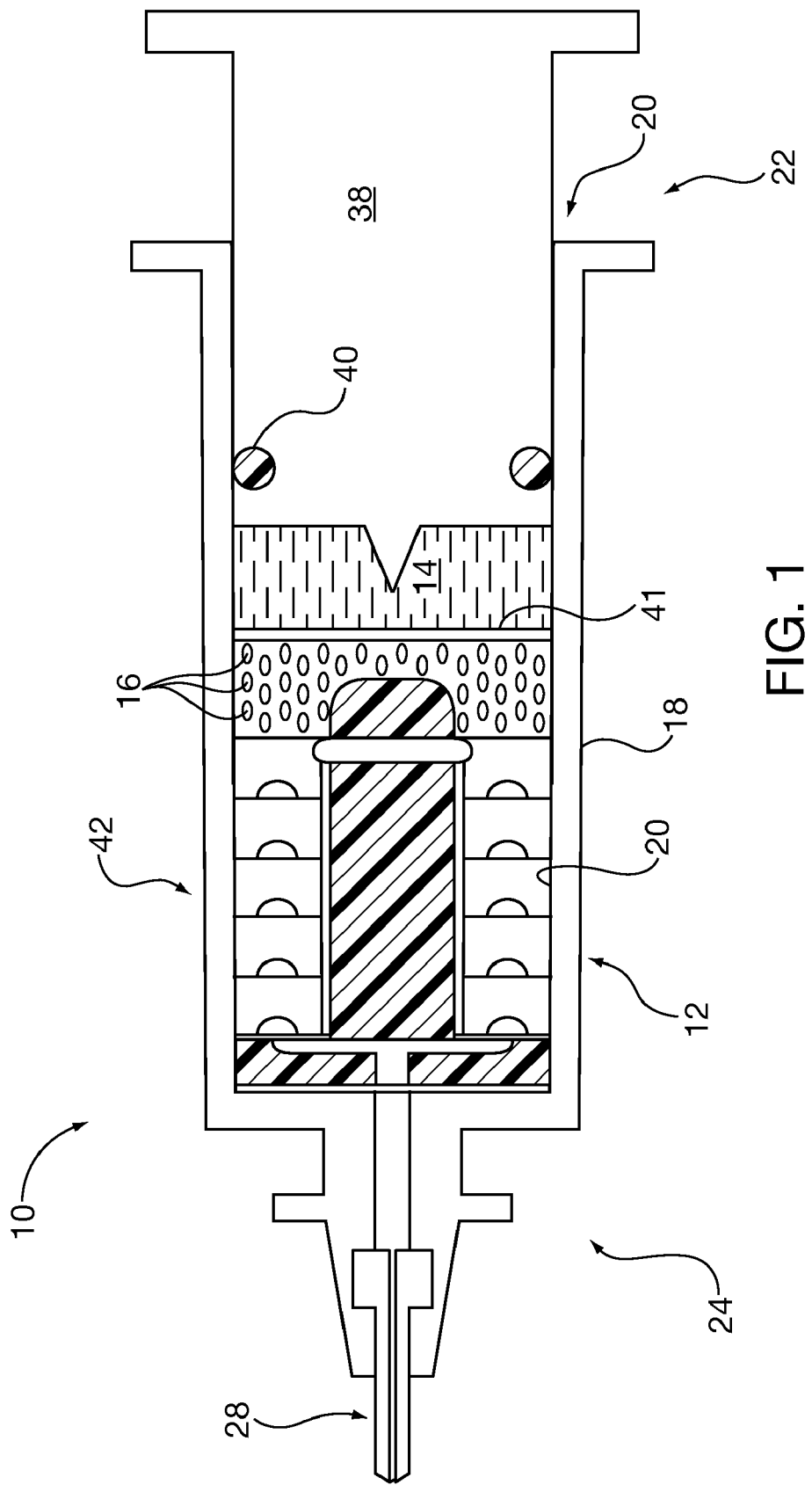
FIG. 1 is a diagrammatic side cross sectional view of an injection device incorporating the components of FIGS. 1-3, shown in a condition which would be seen immediately prior to commencing injection.

FIG. 1 of the drawings shows an injection device 10 for injecting a solution which is generated by blending of a liquid solvent 14 and a solid solute 16 which have been loaded into the injection device 10. The injection device 10 is disposed to hold the liquid solvent 14 and the solid solute 16 apart until the moment of injection, and to intermix or blend within the injection device 10 the liquid solvent 14 and the solid solute 16, thereby generating the solution which is to be injected.

Figure 2:
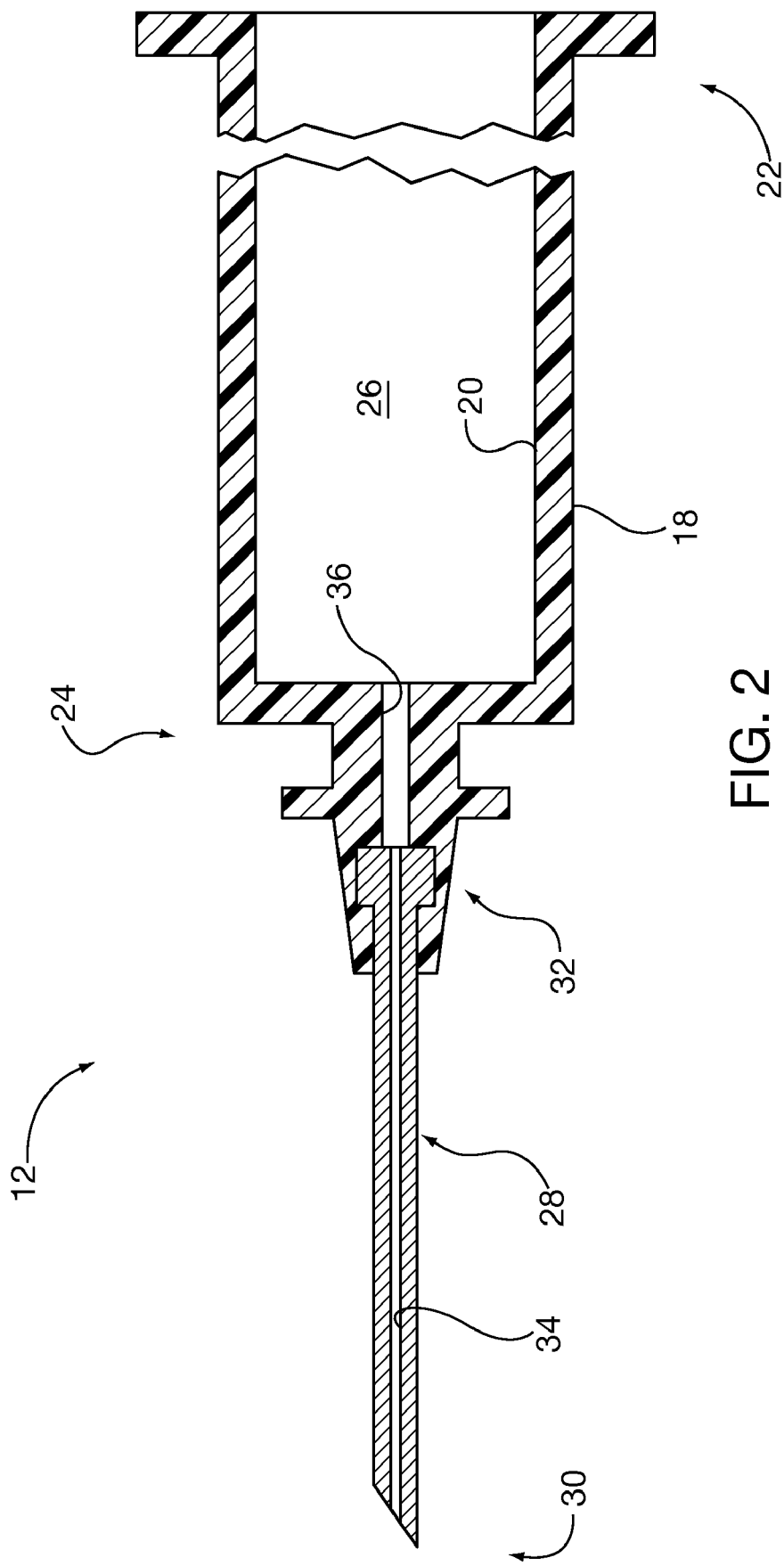
FIG. 2 is a diagrammatic longitudinal cross section of one component of an injection device which may be provided with the benefits of the invention.

The injection device 10 may comprise a barrel 12 which is intended to contain the liquid solvent 14 and the solid solute 16. Referring also to FIG. 2, the barrel 12 may comprise a lateral wall 18 having an interior surface 20, a plunger end 22, and an opposed delivery end 24. A chamber 26 is defined within the interior surface 20 between the plunger end 22 and the delivery end 24. A hollow needle 28 may be coupled to the barrel 12 at the delivery end 24 of the barrel 12. The hollow needle 28 may have a pointed discharge end 30 adapted for example to penetrate the skin of a person for injecting medicaments, an opposed entry end 32, and a bore 34 extending from the entry end 30 to the pointed discharge end 30. The entry end 32 of the hollow needle 28 may be embedded in the constituent material of the delivery end 24 of the barrel 12 or otherwise sturdily coupled thereto.

A fluid pathway 36 formed in the barrel 12 communicates between the chamber 26 and the bore 34 of the hollow needle 28, thereby establishing a continuous path for liquids to traverse when being injected, although the actual path available to the solution being injected is longer and less direct than suggested by FIG. 2.

Figure 3:
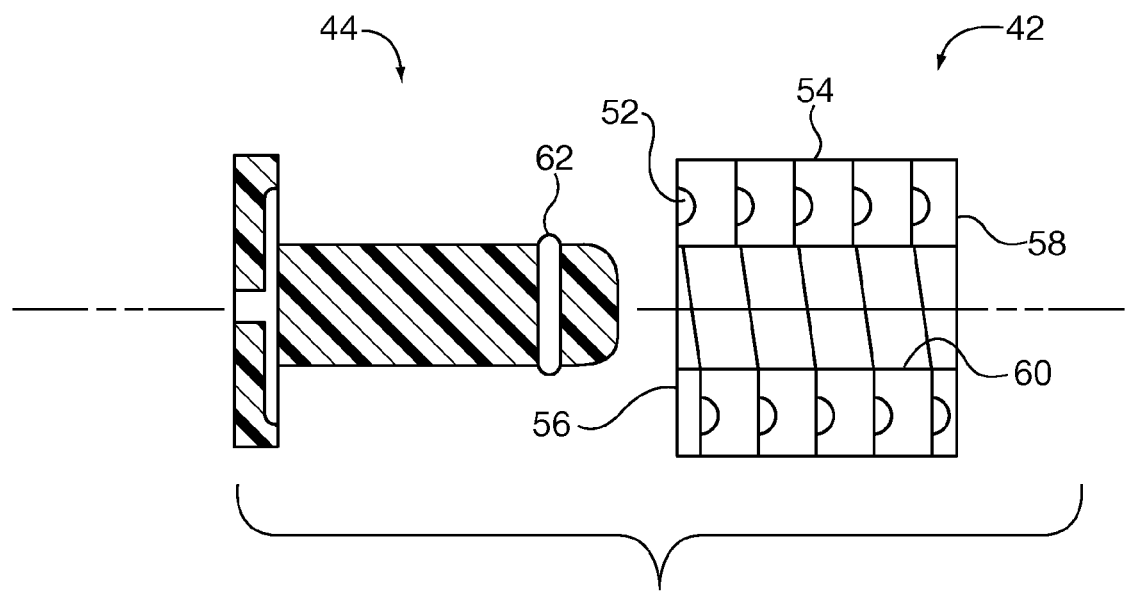
FIG. 3 is a diagrammatic side cross section of two components which may be installed in the component of FIG. 1 to establish an effective flow path for blending.
Figure 4:
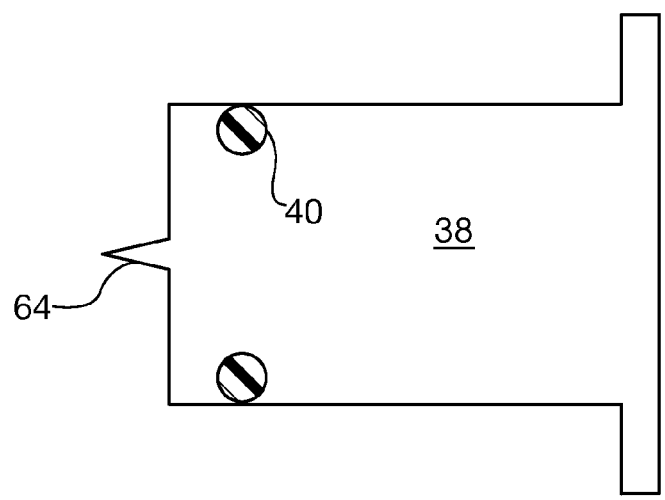
FIG. 4 is a diagrammatic side elevational view of a plunger which may be installed into the component of FIG. 1, and which may work with the components of FIG. 3 after the latter are installed in the component of FIG. 2.

Returning to FIG. 1, the chamber 26 contains components which for better understanding have been shown isolated from the barrel 12 in FIGS. 3 and 4. As seen in FIG. 1, these components include a plunger 38, which may incorporate an O-ring 40 for preventing escape of pressurized solution past the plunger 38. The plunger 38 may be slideably engaged with the interior surface 20 of the barrel at the plunger end 22 of the barrel 12. A barrier which may be of aluminum foil 41 may be disposed within the chamber 26, being interposed between the plunger 38 and two additional components which may combine to establish a flow path for solution which is more intricate and effective in promoting blending of the solid solute 16 in the liquid solvent 14 than would be the case of the open chamber 26 as depicted in FIG. 2.

One of these members is a flow path member 42, the purpose of which is to establish a flow path along which the solution generated by blending of the liquid solvent 14 and the solid solute 16 may flow responsively to urging of the plunger 38 towards the hollow needle 28. The plunger 38 may be generally conventional in construction and purpose, being provided to transfer manual force to liquids being injected by the injection device 10. The flow path member 42 may be disposed between, on one hand, the liquid solvent 14 and the solid solute 16, and on the other hand, the hollow needle 28.

Figure 5:
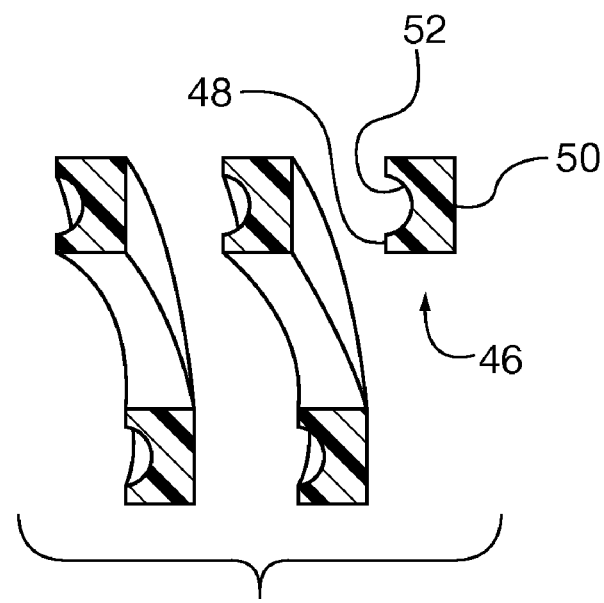
FIG. 5 is a diagrammatic view of one of the components of FIG. 1, shown axially expanded to better reveal its construction.

The nature of the flow path member 42 is best described with reference to FIG. 5. The flow path member 42 may comprise an axially expansible, flexible helical member. When this flexible helical member is viewed in cross section, it may display a generally rectangular perimeter 46 which further comprises a forward axial surface 48 and a rear axial surface 50. The forward axial surface 48 may bear a groove 52. The flow path member 42 may be formed from a somewhat elastic member, such as a synthetic resin, so that it can be manually grasped and axially expanded, as depicted in FIG. 5. In the expanded condition, the flow path member may resemble a coil spring (not shown). It is not the expanded condition that is central to the invention, but rather the compressed condition seen in FIGS. 1 and 3.

Referring particularly to FIG. 3, the flow path member 42 is compressible to form a cylindrical member or configuration, having a continuous cylindrical outer surface 54, a top surface 56, and a bottom surface 58. The top surface 56 is formed by the forward axial surface 48 of the first helical turn of the flow path member 42. The bottom surface 58 is formed by the rear axial surface 50 of the last turn of the flow path member 42. In the compressed configuration of FIGS. 1 and 3, the groove 52 assumes a helical configuration which tracks or mirrors the helical configuration of the flow path member 42. However, compression of the flow path member 42 causes abutment of the forward axial surface 48 and the rear axial surface 50 of adjacent turns of the helix formed by the flow path member 42. This forms a flow path enclosed by the groove 52 of all but the top helical turn and the portion of the rear axial surface 50 which intersects the groove 52 in the adjacent turn of the helix. Access to this flow path is closed to the exterior of the flow path member 42 along the continuous cylindrical outer surface 54. The flow path defined by the groove 52 and the adjacent rear axial surface 50 when the flow path member 42 is compressed is exposed to the exterior of the cylindrical flow path member 42 only at the top surface 56 where the first helical turn intersects the second helical turn and the bottom surface 58 of the cylindrical flow path member 42 where the helix ends.

In the compressed state, the flow path member 42 may form an annular member having the continuous cylindrical outer surface 54, and also a cylindrical inner surface 60. The cylindrical inner surface 60 may be said to define a void at the center of the compressed flow path member 42 between the top surface 56 and the bottom surface 58.

A core member 44 may be provided which cooperates closely with the compressed flow path member 42. The core member 44 may reinforce the flow path member 42 to better maintain the annular configuration shown in FIG. 3. The core member 44 may also contribute to the flow path available to the solution, as will be described hereinafter.

Again referring to FIG. 1, the barrier provided by the aluminum foil 41 separates the liquid solvent 14 from the solid solute 16 until the time of injection. At that time, manual pressure exerted on the plunger 38 from the right thereof in the depiction of FIG. 1 in the direction of the hollow needle 28 will act to open the barrier so as to enable fluid communication between the liquid solvent 14 and the solid solute 16, and subsequent mixing or blending of the two to generate the solution. Blending and propulsion of the liquid solvent 14 towards the hollow needle 28, and of the solution which the liquid solvent 14 becomes as it negotiates the flow path established by the groove 52 are both consequences of the manual pressure imposed on the plunger 38. The solution is constrained against escape from the flow path by close fit of the components of the injection device 10, and by O-rings such as the O-ring 40 of the plunger 38 and an O-ring 62 which may be placed on the core member 44. While sealing arising from any of the various O-rings featured herein contributes to preventing loss of solution such as past the plunger 38, sealing especially constrains the solution against bypassing the flow path member 42, thus assuring effective blending.

The barrier separating the liquid solvent 14 from the solid solute 16 may be opened or breached in any of several ways. Notably, the barrier may be a frangible barrier which is ruptured, it may be deflected to open or expose a flow path, or it may be deformed to open or expose a flow path.

Figure 6:
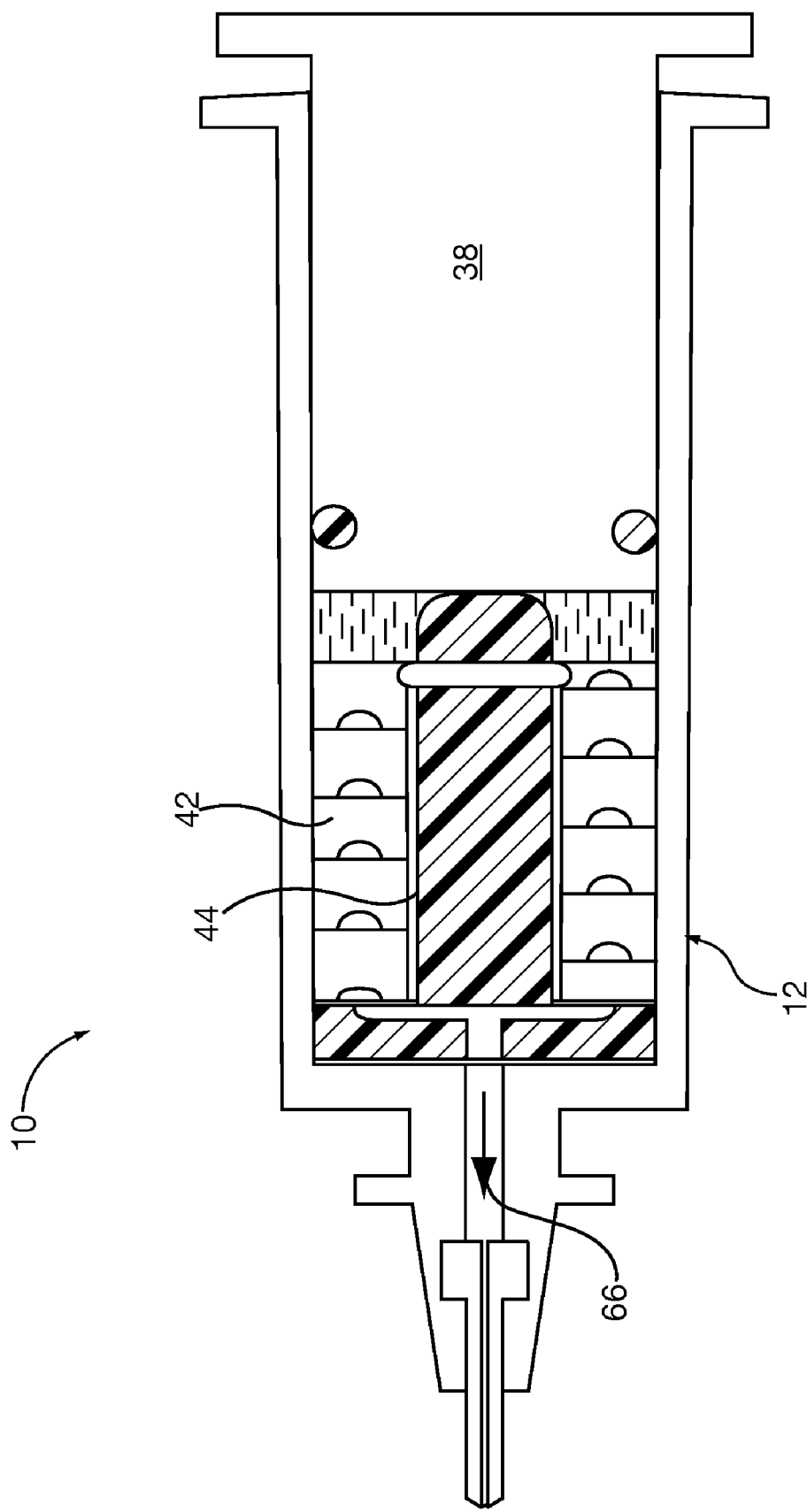
FIG. 6 is a diagrammatic side cross sectional view of FIG. 1, but showing the plunger in a depressed or actuated position which would be seen at or near the completion of injection.

The first option, that of breaking a frangible barrier, is illustrated in FIGS. 1 and 6. FIG. 1 shows an initial position of the plunger 38, wherein injection has not yet been initiated. Injection and blending are initiated by urging the plunger 38 to the left, as depicted in FIG. 1. In FIG. 6, the plunger 38 has been moved such that it has ruptured the aluminum foil 41 and has propelled the liquid solvent 14 past the solid solute 16, through the flow path member 42, through the fluid pathway 36 (see FIG. 2), and out through the bore 34 of the hollow needle 28. The direction of flow is indicated by an arrow 66 in FIG. 6.

The aluminum foil 41 has been ruptured by a pointed finger 64, best seen in FIG. 4, and is not shown in FIG. 6. In other embodiment, the barrier provided by the aluminum foil 41 may be opened so as to enable fluid communication between the liquid solvent 14 and the solid solute 16 by a finger, such as the pointed finger 164 shown in the non-limiting example in FIG. 8. The finger 164 may be disposed to establish actuating contact with the barrier in ways other than by rupturing the barrier.

Figure 7:
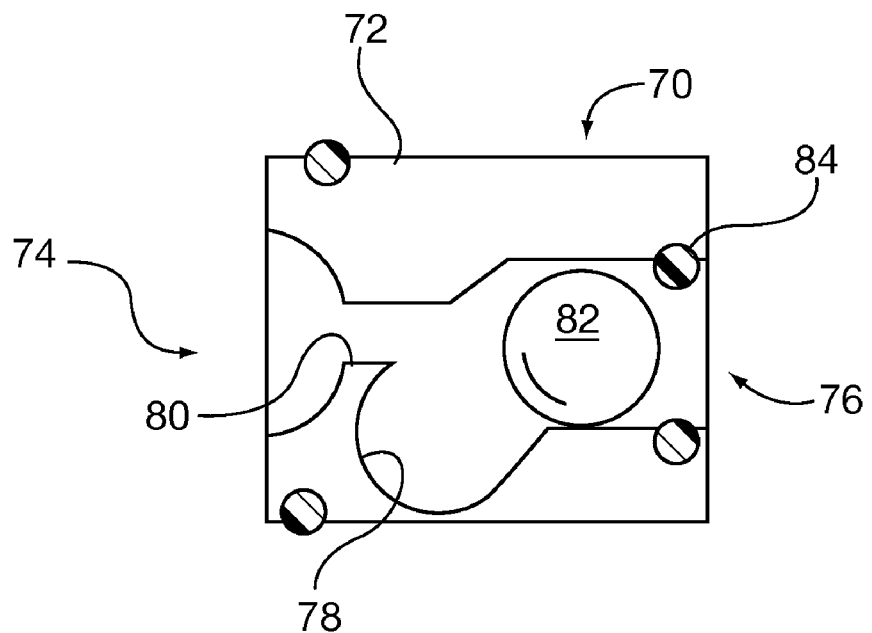
FIG. 7 is a diagrammatic side cross sectional view of a valve which may be employed as an alternative to or in additional to a frangible barrier seen in FIG. 1.

Whereas in FIG. 1 the barrier is frangible and the finger 64 pierces the barrier to open the barrier, a finger 164 may displace a valve to open the barrier. An exemplary valve assembly 70 which may be finger operated is seen in FIG. 7. The valve assembly 70 may comprise a housing 72 bearing a valve flow path 74. The valve flow path 74 may comprise an initial section 76, a second section 78, and a final section 80. A valve 82 may take the form of a sphere, such as a plastic ball 82. The plastic ball 82 may initially occupy the initial section 76, being retained against loss by an O-ring 84.

Figure 8:
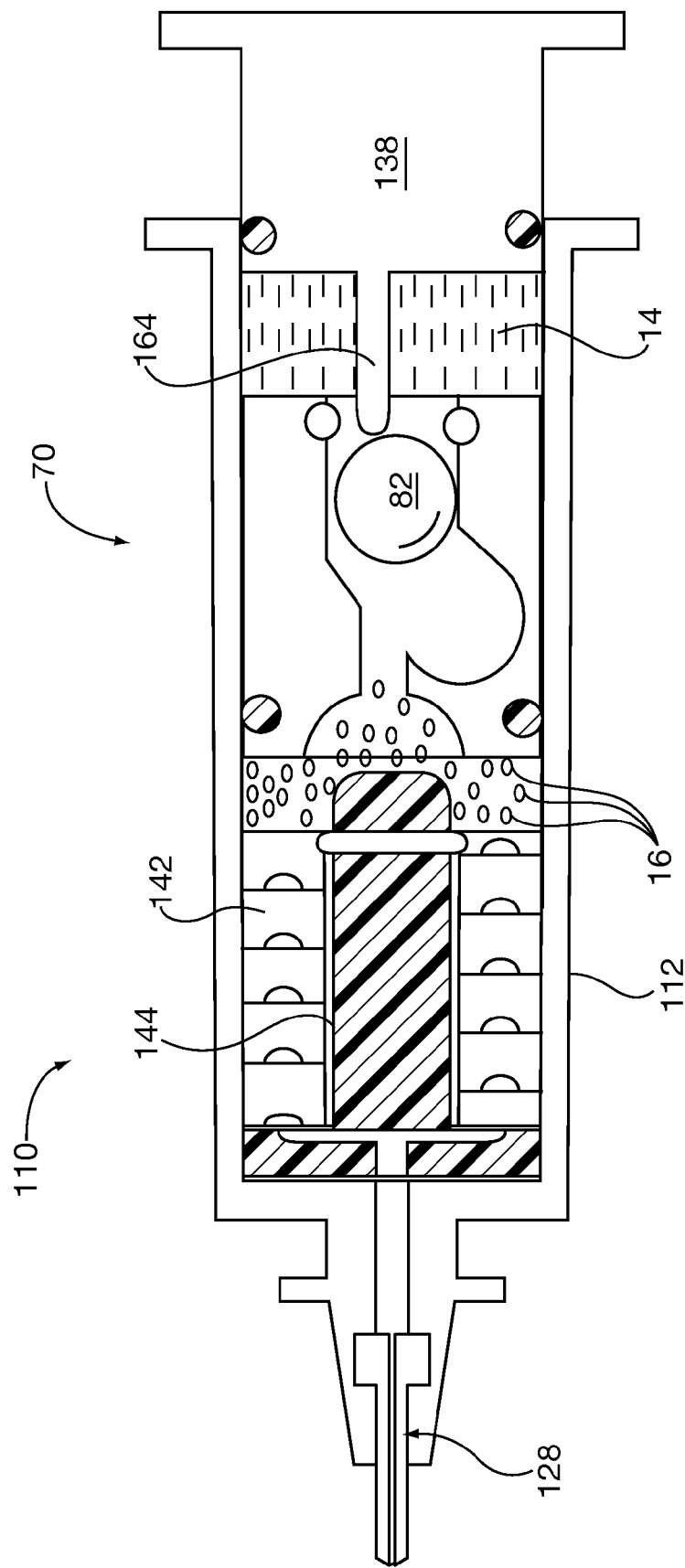
FIG. 8 is a diagrammatic side cross sectional view of an injection device which incorporates the valve of FIG. 7, shown in a condition which would be seen immediately prior to commencing injection.

Turning now to FIG. 8, there is shown an injection device 110 which is generally the structural and functional equivalent of the injection device 10 of FIG. 1, apart from the nature of the barrier. The valve assembly 70 described with reference to FIG. 7 serves as the barrier in the injection device 110. The injection device 110 may have a barrel 112, a hollow needle 128, a flow path member 142, and a core member 144, all of which may be the structural and functional respective equivalents of the barrel 12, the hollow needle 28, the flow path member 142, and the core member 144. A plunger 138 may have a blunt ended finger 164, but in other ways may be the structural and functional equivalent of the plunger 38. A liquid solvent 14 and a solid solute 16 are stored within and on opposing sides of the barrel 112.

Figure 9:
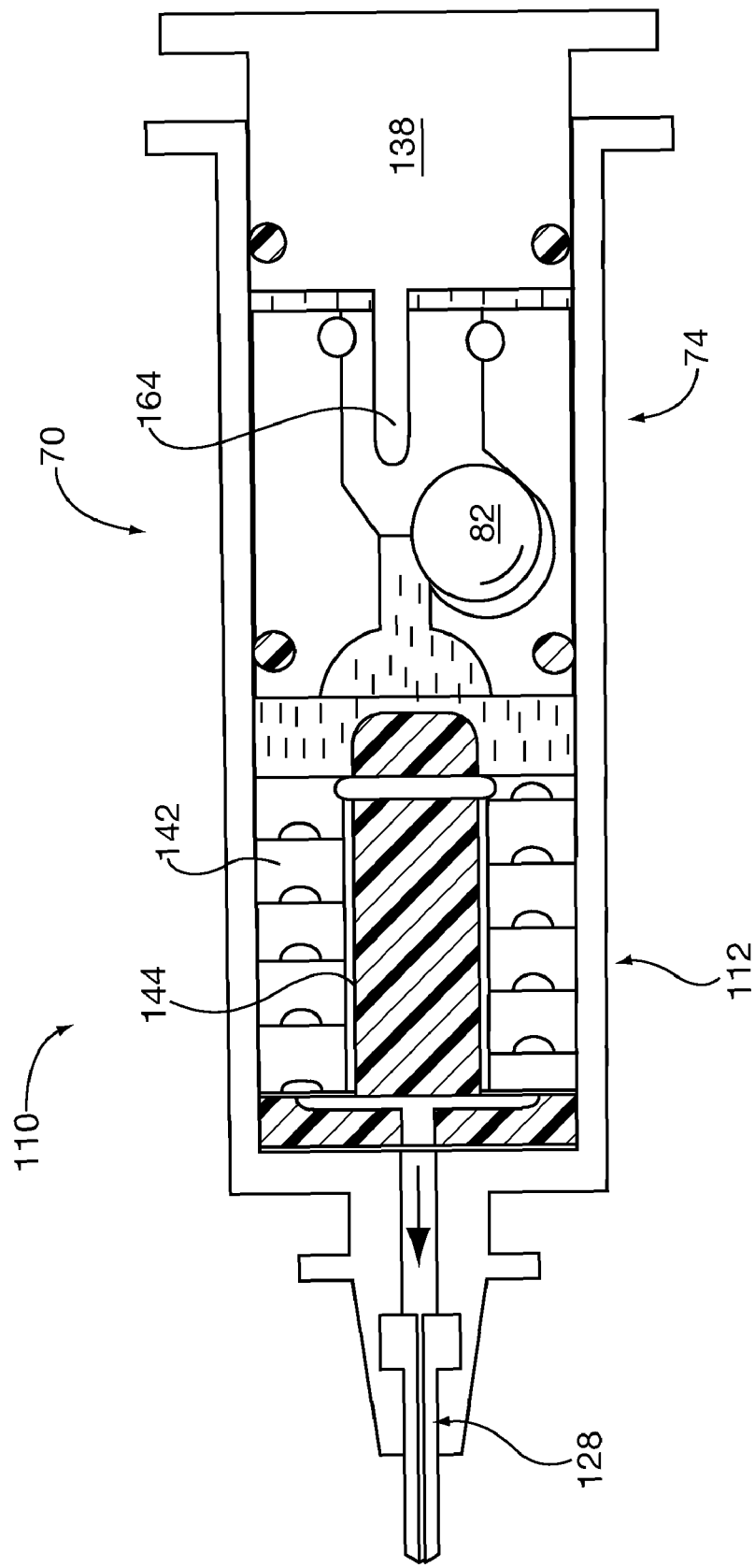
FIG. 9 is a diagrammatic side cross sectional view of FIG. 8, but showing the plunger in a depressed position which would be seen at or near the completion of injection.

In FIG. 8, the finger 164 is approaching the point of contact with the plastic ball 82. As the finger 164 continues to advance to the left, as seen in FIG. 9, the liquid solvent 14 is propelled through the valve flow path 74 into blending contact with the solid solute 16. The liquid solvent 14 and the solid solute 16 are then propelled through the flow path member 142, where dissolution is furthered prior to discharge of solution through the hollow needle 128.

In summary, the barrier comprises the valve assembly 70 the plastic ball 82 of which is displaced non-axially by the finger 164 to open the barrier.

FIGS. 10 and 11 illustrate a valve assembly 270 wherein the valve 282 is axially shiftable to expose a flow path 274 when the valve 282 is axially shifted to open the barrier provided by the valve assembly 270. The valve assembly 270 may be substituted in an injection device according to at least one aspect of the invention, such as the injection device 110. In this example, the valve assembly 70 may be omitted, with the valve assembly 270 installed thereinstead.

It should be noted that in the injection devices 10 and 110, and also with reference to the valve 270, the barrier provided respectively by the aluminum foil 41, the valve 70, or the valve 270 may be operated by fluid pressure developed by the associated plungers 38 or 138 when the latter are moved as described priorly with respect to mechanical action.

FIGS. 12 and 13 show a further type of barrier. In FIG. 12, a barrier is established by a flexible rubbery member 370, which may be arranged to close the internal passage 374 if the rubbery member 370 is not acted on by an external element. Such an external element may be provided by a suitably configured finger 364 which may be part of an associated plunger (not shown in its entirety), such as the plunger 38 or 138. The finger 364 may have structure such as a wing 365 for spreading open the rubbery member 370 to open the barrier established thereby to fluid communication enabling a liquid solvent such as the liquid solvent 14 to pass and blend with a solid solute such as the solid solute 16, as occurs with the injection devices 10 and 110.

Figure 14:
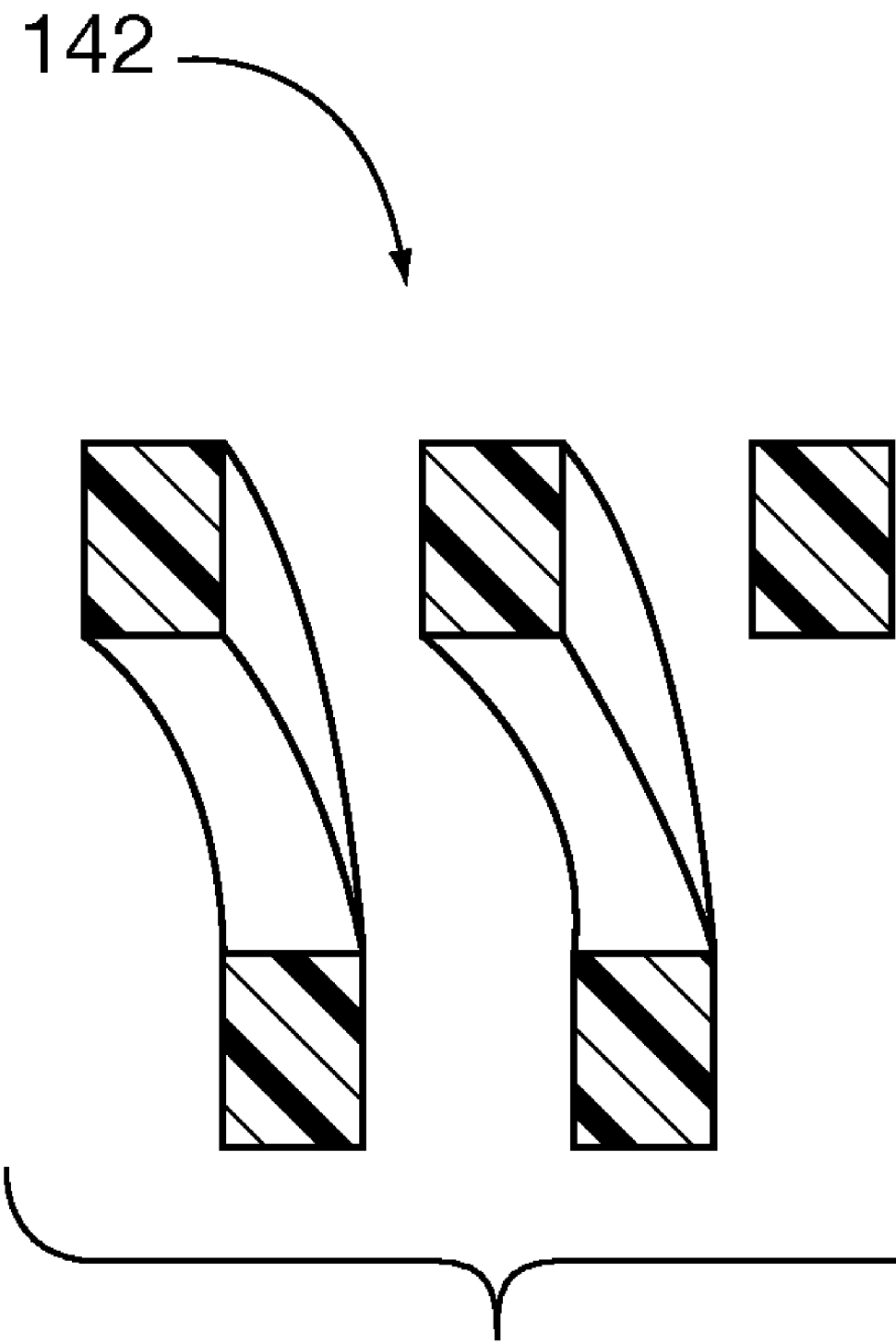
FIG. 14 is similar to FIG. 5, but shows a component corresponding to yet differently constructed compared to that of FIG. 5.

FIG. 14 shows a flow path member 142 which performs the same function as the flow path member 42 of FIG. 5. The difference is that the flow path member 142 has no groove such as the groove 52 of FIG. 5. The flow path member 142 is nonetheless operable because pressure imposed on fluid of the solution being injected slightly spreads apart adjacent coils of the flow path member, thereby establishing a flow path between adjacent coils which corresponds to the flow path which occupies the groove 52 of FIG. 5.

The nature of the flow path member 42 is best described with reference to FIG. 5. The flow path member 42 may comprise an axially expansible, flexible helical member. When this flexible helical member is viewed in cross section, it may display a generally rectangular perimeter 46 which further comprises a forward axial surface 48 and a rear axial surface 50. The forward axial surface 48 may bear a groove 52. The flow path member 42 may be formed from a somewhat elastic member, such as a synthetic resin, so that it can be manually grasped and axially expanded, as depicted in FIG. 5. In the expanded condition, the flow path member may resemble a coil spring (not shown). It is not the expanded condition that is central to the invention, but rather the compressed condition seen in FIGS. 1 and 3.

Referring particularly to FIG. 3, the flow path member 42 is compressible to form a cylindrical member or configuration, having a continuous cylindrical outer surface 54, a top surface 56, and a bottom surface 58. The top surface 56 is formed by the forward axial surface 48 of the first helical turn of the flow path member 42. The bottom surface 58 is formed by the rear axial surface 50 of the last turn of the flow path member 42. In the compressed configuration of FIGS. 1 and 3, the groove 52 assumes a helical configuration which tracks or mirrors the helical configuration of the flow path member 42. However, compression of the flow path member 42 causes abutment of the forward axial surface 48 and the rear axial surface 50 of adjacent turns of the helix formed by the flow path member 42. This forms a flow path enclosed by the groove 52 of all but the top helical turn and the portion of the rear axial surface 50 which intersects the groove 52 in the adjacent turn of the helix. Access to this flow path is closed to the exterior of the flow path member 42 along the continuous cylindrical outer surface 54. The flow path defined by the groove 52 and the adjacent rear axial surface 50 when the flow path member 42 is compressed is exposed to the exterior of the cylindrical flow path member 42 only at the top surface 56 where the first helical turn intersects the second helical turn and the bottom surface 58 of the cylindrical flow path member 42 where the helix ends.

In the compressed state, the flow path member 42 may form an annular member having the continuous cylindrical outer surface 54, and also a cylindrical inner surface 60. The cylindrical inner surface 60 may be said to define a void at the center of the compressed flow path member 42 between the top surface 56 and the bottom surface 58.

The invention may be thought of as an injection device, such as the injection devices 10 and 110, or alternatively, as a flow path member for establishing a flow path along which a solution generated by blending of a liquid solvent and a solid solute may flow, such as the flow path member 42 or 142.

The inventive injection device may be thought of as incorporating a barrier which is opened by rupturing the barrier, as seen in the injection device 10. Alternatively, the barrier may be deflected to open, as seen with the valves 70 and 270. In a further variation, the barrier may be deformed to open, as seen with the rubbery member 370.

The present invention is susceptible to modifications and variations which may be introduced thereto without departing from the inventive concepts. For example, although the invention has been described with respect to a syringe, the novel principles apply equally to other devices, such as injection devices known as autoinjectors.

It would be possible to provide a helical flow path member such as the flow path member 42 which has no central void, or alternatively to permit the flow path member to function on its own in the absence of a core reinforcing member such as the core member 44.

Location of a point such as that seen on the pointed finger 66 of FIG. 4 may be relocated. For example, the core member 44 may be provided with a corresponding point to pierce a frangible barrier such as the aluminum foil 41.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. An injection device comprising:
    a barrel disposed to contain a liquid solvent and a solid solute, comprising a lateral wall having an interior surface, a plunger end, an opposed delivery end, and a chamber defined within the interior surface between the plunger end and the delivery end;
    a hollow needle coupled to the barrel at the delivery end of the barrel, having a pointed discharge end, an opposed entry end, and a bore extending from the entry end to the pointed discharge end;
    a plunger which is slidably engaged with the interior surface of the barrel at the plunger end of the barrel;
    a barrier disposed within the chamber of the barrel, which is disposed to separate the liquid solvent and the solid solute;
    means for opening the barrier so as to enable fluid communication between the liquid solvent and the solid solute; and
    a flow path member disposed between, on one hand, the liquid solvent and the solid solute, and on the other hand, the hollow needle, which flow path member establishes a flow path along which a solution generated by blending of the liquid solvent and the solid solute may flow responsively to urging of the plunger towards the hollow needle, wherein
    the flow path member comprises an axially expansible, flexible member having a helical configuration including a forward axial surface having a groove tracking the helical configuration, a rear axial surface, a first helical turn, and a last helical turn; and
    the flow path member is compressible to form a cylindrical member having a continuous cylindrical outer surface, a top surface formed by the forward axial surface of the first helical turn, and a bottom surface formed by the rear axial surface of the last helical turn; and the flow path passes through the cylindrical member and is defined by the intersection of the groove and the rear axial surface and when passing through the cylindrical member, the flow path is exposed to the exterior of the cylindrical member only at the top surface and the bottom surface.

2. The injection device according to claim 1, wherein
    the flow path member is compressible to form an annular member having a continuous cylindrical outer surface, a cylindrical inner surface defining a void between the top surface and the bottom surface of the cylindrical member when the cylindrical member is compressed, and
    the injection device further comprises a core member disposed to fill the void and to cooperate closely with the cylindrical inner surface of the flow path member when the flow path member is compressed.

3. The injection device according to claim 1, further comprising at least one O-ring and, wherein the a flow path passes through the barrel past the barrier, and through the hollow needle, a solution is generated by blending of the liquid solvent and the solid solute, and the at least one O-ring constrains the solution to flow within the flow path and against bypassing the flow path member.

4. The injection device according to claim 1, wherein the means for opening the barrier so as to enable fluid communication between the liquid solvent and the solid solute comprises a finger disposed to establish actuating contact with the barrier.

5. The injection device according to claim 4, wherein the barrier is frangible and the finger pierces the barrier to open the barrier.

6. The injection device according to claim 4, wherein the barrier comprises a valve and the finger displaces the valve to open the barrier.

7. The injection device according to claim 6, further comprising an axis, and wherein the valve is axially shiftable and exposes a flow path when axially shifted to open the barrier.

8. The injection device according to claim 6, further comprising an axis, and wherein the valve comprises a ball which is moved non-axially by the finger to open the barrier.

9. The injection device according to claim 1, wherein the means for opening the barrier so as to enable fluid communication between the liquid solvent and the solid solute operates responsively to pressure exerted by the plunger when the plunger is urged in a direction towards the hollow needle.

10. The injection device according to claim 9, wherein the barrier comprises a valve and the valve is displaced by fluid pressure to open the barrier when the plunger is urged in a direction towards the hollow needle.

11. The injection device according to claim 10, further comprising an axis, and wherein the valve is axially shiftable and exposes a flow path when axially shifted to open the barrier responsively to fluid pressure when the plunger is urged in a direction towards the hollow needle.

12. The injection device according to claim 10, further comprising an axis, and wherein the valve comprises a ball which is moved non-axially by fluid pressure to open the barrier when the plunger is urged in a direction towards the hollow needle.

13. The injection device according to claim 10, further comprising at least one O-ring disposed to constrain a solution generated by blending of the liquid solvent and the solid solute against bypassing the valve.

14. A flow path member for establishing a flow path along which a solution generated by blending of a liquid solvent and a solid solute may flow, comprising an axially expansible, flexible member having a helical configuration including a forward axial surface having a groove tracking the helical configuration, a rear axial surface, a first helical turn, and a last helical turn; and
wherein the flow path member is compressible to form a cylindrical member having a continuous cylindrical outer surface, a top surface formed by the forward axial surface of the first helical turn, and a bottom surface formed by the rear axial surface of the last helical turn; the cylindrical member including a flow path defined by the intersection of the groove and the rear axial surface and exposed to the exterior of the cylindrical member only at the top surface and the bottom surface.

15. The flow path member according to claim 14, wherein the flow path member is compressible to form an annular member having a continuous cylindrical outer surface, a cylindrical inner surface defining a void between the top surface and the bottom surface.

16. The flow path member according to claim 14, wherein the flow path member includes a second helical turn, and the flow path begins at the intersection of the first helical turn and the second helical turn and ends at the end of the last helical turn.

* * * * *